(12) United States Patent
Massonne et al.

(10) Patent No.: US 8,389,740 B2
(45) Date of Patent: Mar. 5, 2013

(54) PROCESS FOR PREPARING IONIC LIQUIDS BY ANION EXCHANGE

(75) Inventors: Klemens Massonne, Bad Duerkheim (DE); Michael Siemer, Mannheim (DE); Werner Mormann, Siegen (DE); Wei Leng, Lemfoerde (DE)

(73) Assignee: BASF SE, Ludwigshafen (DE)

( * ) Notice: Subject to any disclaimer, the term of this patent is extended or adjusted under 35 U.S.C. 154(b) by 409 days.

(21) Appl. No.: 12/682,876

(22) PCT Filed: Oct. 31, 2008

(86) PCT No.: PCT/EP2008/064794
§ 371 (c)(1),
(2), (4) Date: Apr. 13, 2010

(87) PCT Pub. No.: WO2009/059934
PCT Pub. Date: May 14, 2009

(65) Prior Publication Data
US 2010/0217010 A1     Aug. 26, 2010

(30) Foreign Application Priority Data
Nov. 8, 2007  (DE) .......................... 10 2007 053 630

(51) Int. Cl.
  *C07D 233/54*   (2006.01)
  *C07C 211/62*   (2006.01)
  *C07C 279/02*   (2006.01)
(52) U.S. Cl. ...................... 548/335.1; 564/230; 564/281
(58) Field of Classification Search .................. 548/335; 564/230, 281
See application file for complete search history.

(56) References Cited

U.S. PATENT DOCUMENTS

| | | |
|---|---|---|
| 5,077,414 A | 12/1991 | Arduengo, III |
| 5,182,405 A | 1/1993 | Arduengo, III |
| 2008/0251759 A1 | 10/2008 | Kalb et al. |
| 2010/0137643 A1 | 6/2010 | Tishkov et al. |

FOREIGN PATENT DOCUMENTS

| | | |
|---|---|---|
| WO | 91 14678 | 10/1991 |
| WO | 2005 021484 | 3/2005 |
| WO | WO 2005/021484 A2 * | 3/2005 |
| WO | 2006 027070 | 3/2006 |

OTHER PUBLICATIONS

U.S. Appl. No. 12/747,372, filed Jun. 10, 2010, Degen, et al.

* cited by examiner

*Primary Examiner* — Kamal Saeed
*Assistant Examiner* — Janet L Coppins
(74) *Attorney, Agent, or Firm* — Oblon, Spivak, McClelland, Maier & Neustadt, L.L.P.

(57) ABSTRACT

Process for preparing salts of the formula I $$(B^+)_n x A^{y-}$$

where
B is a cation comprising at least one nitrogen atom,
A is an anion and
n is an integer from 1 to 3,
x and y are each an integer from 1 to 3 and the product of x and y is equal to n,
by reacting salts of the formula II $$(B^+)_n x C^{y-}$$

where B and n, x and y are as defined above and C is a compound which has one or more carboxylate groups (referred to as carboxylate for short) and is different from A, with the ammonium salt of the anion A or with the protic acid of the anion A in the presence of ammonia.

12 Claims, No Drawings

PROCESS FOR PREPARING IONIC LIQUIDS BY ANION EXCHANGE

The invention relates to a process for preparing salts of the formula I

where
B is a cation comprising at least one nitrogen atom,
A is an anion and
n is an integer from 1 to 3,
x and y are each an integer from 1 to 3 and the product of x and y is equal to n, by reacting salts of the formula II

where B and n, x and y are as defined above and C is a compound which has one or more carboxylate groups (referred to as carboxylate for short) and is different from A, with the ammonium salt of the anion A or with the protic acid of the anion A in the presence of ammonia.

Salts having a melting point of less than 200° C., in particular a melting point of less than 100° C., are referred to as ionic liquids. Ionic liquids which are liquid at room temperature are of particular interest.

There are various methods of preparing ionic liquids. Ionic liquids having ammonium cations and carboxylate anions can, for example, be prepared by the methods described in WO 2005/021484 (carbonate method) or in WO 91/14678 (Arduengo process). Ionic liquids having anions other than carboxylate anions can be obtained by subsequent replacement of the anion.

WO 2006/027070 describes such an anion exchange using a protic acid having a pKa of ≦14. Complete anion exchange cannot be achieved by the process described or can be achieved only by means of complicated process measures, e.g. multiple distillation.

It is therefore an object of the present invention to provide a simple and effective process for preparing salts, in particular ionic liquids, by anion exchange.

We have accordingly found the process defined at the outset.

Regarding the Cation B of the Salts of the Formula I

Salts of the formula I above are prepared in the process of the invention.

The cation B in formula I comprises at least one nitrogen atom. B is preferably a guanidinium compound or an ammonium compound. For the present purposes, the term ammonium compound refers both to compounds having four substituents on the nitrogen atom and to ring systems having at least one nitrogen atom and a delocalized positive charge.

Suitable guanidinium cations have the general formula (IV)

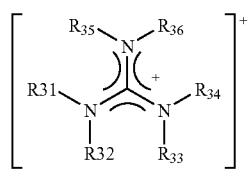

where
the radicals R32 to R36 are each, independently of one another, a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups and the radicals R33 and R35 may, independently of one another, also be hydrogen; or two adjacent radicals R33 together with R34; or R35 together with R36 form a divalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups and the remaining radicals are as defined above;
and the radical R31 is a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups.

Suitable quaternary ammonium cations are, for example, those of the formula (V)

where
R7 together with R8 forms a divalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups; or
R7 together with R8 and R9 forms a trivalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups; and the remaining radicals are each a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups, with R6 also being able to be hydrogen.

Preferred cations B comprise a heterocyclic ring system having at least one nitrogen atom.

Particularly preferred cations B comprise an aromatic, heterocyclic ring system having at least one nitrogen atom and a delocalized positive charge.

Suitable cations are, in particular, derivatives of imidazolium, of imidazolinium, of pyrazolium, of pyrazolinium and of pyridinium.

The cation is very particularly preferably an imidazolium cation.

Suitable imidazolium cations preferably have the general formula (III)

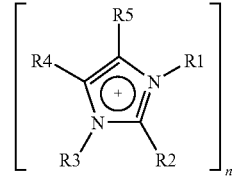

where
R1 and R3 are each, independently of one another, an organic radical having from 1 to 20 carbon atoms and
R2, R4 and R5 are each, independently of one another, an H atom or an organic radical having from 1 to 20 carbon atoms.

Preference is given to R1 and R3 each being, independently of one another, an organic radical comprising from 1 to 10 carbon atoms. The radical is particularly preferably a hydrocarbon group which does not have any further heteroatoms, e.g. a saturated or unsaturated aliphatic group, an aromatic group or a hydrocarbon group which has both aromatic and aliphatic parts. The radical is very particularly preferably a C1-C10-alkyl group, a C1-C10-alkenyl group, e.g. an allyl group, a phenyl group, a benzyl group. In particular, it is a C1-C4-alkyl group, e.g. a methyl group, ethyl group, propyl group, i-propyl group or n-butyl group.

Preference is given to R2, R4 and R5 each being, independently of one another, an H atom or an organic group comprising from 1 to 10 carbon atoms. Particular preference is given to R2, R4 and R5 each being an H atom or a hydrocarbon group which does not have any further heteroatoms, e.g. an aliphatic group, an aromatic group or a hydrocarbon group which has both aromatic and aliphatic parts. Very particular preference is given to R2, R4 and R5 each being, independently of one another, an H atom or a C1-C10-alkyl group, a phenyl group or a benzyl group. In particular, they are each an H atom or a C1- to C4-alkyl group, e.g. a methyl group, ethyl group, propyl group, i-propyl group or n-butyl group.

Suitable imidazolinium cations preferably have the general formula (VI)

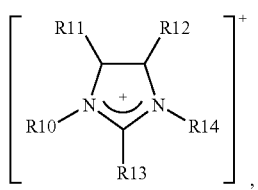

(VI)

where
the radicals R11 to R14 are each, independently of one another, a sulfo group or a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups and the radicals R11 to R13 may, independently of one another, also be hydrogen, halogen or a functional group and the radical R14 may also be hydrogen; or
two adjacent radicals R11 together with R12; or R12 together with R14; or R14 together with R13 form a divalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups and the remaining radicals are as defined above;
and the radical R10 is a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups.

Suitable pyrazolium cations preferably have the general formula (VII)

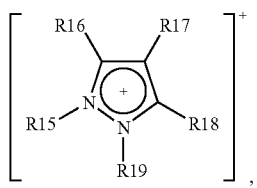

(VII)

where
the radicals R16 to R19 are each, independently of one another, a sulfo group or a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups and the radicals R16 to R18 may, independently of one another, also be hydrogen, halogen or a functional group and the radical R19 may also be hydrogen; or
two adjacent radicals R16 together with R17; or R17 together with R18; or R18 together with R19 form a divalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups and the remaining radicals are as defined above; and the radical R15 is a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups.

Suitable pyrazolinium cations preferably have the general formula (VIII)

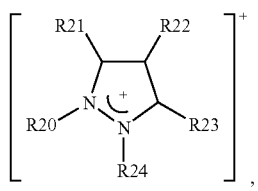

(VIII)

where
the radicals R21 to R24 are each, independently of one another, a sulfo group or a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups and the radicals R21 to R23 may, independently of one another, also be hydrogen, halogen or a functional group and the radical R24 may also be hydrogen; or
two adjacent radicals R21 together with R22; or R22 together with R24; or R24 together with R23 form a divalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups and the remaining radicals are as defined above;
and the radical R20 is a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups.

Suitable pyridinium cations preferably have the general formula (IX)

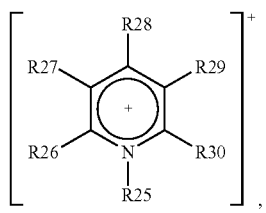

(IX)

where
the radicals R26 to R30 are each, independently of one another, hydrogen, halogen, a functional group or a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups; or two adjacent radicals R26 together with R27; or R27 together with R28; or R28 together with R29 or R29 together with R30 form a divalent, carbon-comprising organic, saturated or unsaturated, acyclic or cyclic, aliphatic, aromatic or araliphatic radical which has from 1 to 30 carbon atoms and may be unsubstituted or interrupted or substituted by from 1 to 5 heteroatoms or functional groups and the remaining radicals are as defined above;

and the radical R25 is a carbon-comprising organic, saturated or unsaturated, acyclic or cyclic, aliphatic, aromatic or araliphatic radical which has from 1 to 20 carbon atoms and may be unsubstituted or interrupted or substituted by from 1 to 5 heteroatoms or functional groups.

Regarding the Anion A of the Salts of the Formula I

In the process of the invention, a carboxylate anion (see formula II) is replaced by another anion. If A in formula I is a carboxylate, it should be a different carboxylate than that in formula II.

The anion A can be monovalent, divalent or trivalent. A is preferably monovalent (y=1). Accordingly, x is then also 1 and n is 1.

In particular, the anion is
fluoride; hexafluorophosphate; hexafluoroarsenate; hexafluoroantimonate; trifluoroarsenate; nitrite; nitrate; sulfate; hydrogensulfate; carbonate; hydrogencarbonate; phosphate; hydrogenphosphate; dihydrogenphosphate, vinylphosphonate, dicyanamide, bis(pentafluoroethyl)phosphinate, tris(pentafluoroethyl)trifluorophosphate, tris(heptafluoropropyl)trifluorophosphate, bis[oxalato(2-)]borate, bis[salicylato(2-)]borate, bis[1,2-benzenediolato(2-)-O,O'] borate, tetracyanoborate, tetracarbonylcobaltate;

tetrasubstituted borate, in particular of the general formula (Va) $[BR^aR^bR^cR^d]^-$, where $R^a$ to $R^d$ are each, independently of one another, fluorine or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogen;

organic sulfonate, in particular of the general formula (Vb) $[R^e—SO_3]^-$, where $R^e$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogen;

carboxylate, in particular of the general formula (Vc) $[R^f—COO]^-$, where $R^f$ is hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups (which may also be further carboxylate groups) or halogen;

(fluoroalkyl)fluorophosphate, in particular of the general formula (Vd) $[PF_x(C_yF_{2y+1-z}H_z)_{6-x}]^-$, where $1 \leq x \leq 6$, $1 \leq y \leq 8$ and $0 \leq z \leq 2y+1$;

imide, in particular of the general formula (Ve) $[R^g—SO_2—N—SO_2—R^h]^-$, (Vf) $[R^i—SO_2—N—CO—R^j]^-$ or (IVg) $[R^k—CO—N—CO—R^l]^-$, where $R^g$ to $R^l$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogen;

methide, in particular of the general formula (Vh)

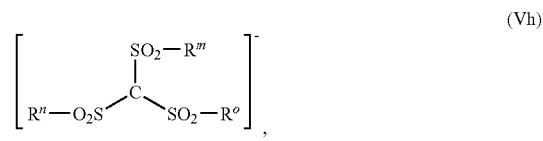

where $R^m$ to $R^o$ are each, independently of one another, hydrogen or a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogen;

organic sulfate, in particular of the general formula (Vi) $[R^PO—SO_3]^-$, where $R^P$ is a carbon-comprising organic, saturated or unsaturated, acyclic or cyclic, aliphatic, aromatic or araliphatic radical which has from 1 to 30 carbon atoms and may comprise one or more heteroatoms and/or be substituted by one or more functional groups or halogen, or halometalate, in particular of the general formula (Vj) $[M_qHal_r]^{s-}$, where M is a metal and Hal is fluorine, chlorine, bromine or iodine, q and r are positive integers and indicate the stoichiometry of the complex and s is a positive integer and indicates the charge on the complex.

Possible heteroatoms in the above formulae are in principle all heteroatoms which are formally able to replace a —$CH_2$—, a —CH= or a =C= group. If the carbon-comprising radical comprises heteroatoms, preference is given to oxygen, nitrogen, sulfur, phosphorus and silicon. Preferred groups are, in particular, —O—, —S—, —SO—, —$SO_2$—, —NR—, —N=, —PR—, —$PR_2$ and —$SiR_2$—, where the radicals R are each the remaining part of the carbon-comprising radical.

Possible functional groups in the above formulae are in principle all functional groups which can be bound to a carbon atom or a heteroatom. Suitable examples are —OH (hydroxy), =O (in particular as carbonyl group), —$NH_2$ (amino), =NH (imino), —COOH (carboxy), —$CONH_2$ (carboxamide) and —CN (cyano). Functional groups and heteroatoms can also be directly adjacent, so that combinations of a plurality of adjacent atoms such as —O-(ether), —S-(thioether), —COO-(ester), —CONH-(secondary amide) or —CONR-(tertiary amide) also being comprised.

As halogens, mention may be made of fluorine, chlorine, bromine and iodine.

When the radicals $R^a$ to $R^d$ in the tetrasubstituted borate (Va), the radical $R^e$ in the organic sulfonate (Vb), the radical $R^f$ in the carboxylate (Vc), the radicals $R^g$ to $R^l$ in the imides (Ve), (Vf) and (Vg), the radicals $R^m$ to $R^o$ in the methide (Vh) and the radical $R^P$ in the organic sulfate (Vi) are carbon-comprising organic, saturated or unsaturated, acyclic or cyclic, aliphatic, aromatic or araliphatic radicals having from 1 to 30 carbon atoms, they are, independently of one another, preferably $C_1$-$C_{30}$-alkyl and its aryl-, heteroaryl-, cycloalkyl-, halogen-, hydroxy-, amino-, carboxy-, formyl-, —O—, —CO—, —CO—O— or —CO—N<substituted components, for example methyl, ethyl, 1-propyl, 2-propyl, 1-butyl, 2-butyl, 2-methyl-1-propyl (isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl(benzyl), diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl, methoxy, ethoxy, formyl, acetyl or $C_nF_{2(n-a)+(1-b)}H_{2a+b}$ where $n \leq 30$, $0 \leq a \leq n$ and $b=0$ or $1$ (for example $CF_3$, $C_2F_5$, $CH_2CH_2$—$C_{(n-2)}F_{2(n-2)+1}$, $C_6F_{13}$, $C_8F_{17}$, $C_{10}F_{21}$, $C_{12}F_{25}$);

$C_3$-$C_{12}$-cycloalkyl and its aryl-, heteroaryl-, cycloalkyl-, halogen-, hydroxy-, amino-, carboxy-, formyl-, —O—, —CO— or —CO—O-substituted components, for example cyclopentyl, 2-methyl-1-cyclopentyl, 3-methyl-1-cyclopentyl, cyclohexyl, 2-methyl-1-cyclohexyl, 3-methyl-1-cyclohexyl, 4-methyl-1-cyclohexyl or $C_nF_{2(n-a)-(1-b)}H_{2a-b}$ where $n \leq 30$, $0 \leq a \leq n$ and $b=0$ or $1$;

$C_2$-$C_{30}$-alkenyl and its aryl-, heteroaryl-, cycloalkyl-, halogen-, hydroxy-, amino-, carboxy-, formyl-, —O—, —CO— or —CO—O-substituted components, for example 2-propenyl, 3-butenyl, cis-2-butenyl, trans-2-butenyl or $C_nF_{2(n-a)-(1-b)}H_{2a-b}$ where $n \leq 30$, $0 \leq a \leq n$ and $b=0$ or $1$;

$C_3$-$C_{12}$-cycloalkenyl and its aryl-, heteroaryl-, cycloalkyl-, halogen-, hydroxy-, amino-carboxy-, formyl-, —O—, —CO— or —CO—O-substituted components, for example 3-cyclopentenyl, 2-cyclohexenyl, 3-cyclohexenyl, 2,5-cyclohexadienyl or $C_nF_{2(n-a)-(1-b)}H_{2a-3b}$ where $n \leq 30$, $0 \leq a \leq n$ and $b=0$ or $1$; and aryl or heteroaryl having from 2 to 30 carbon atoms and its alkyl-, aryl-, heteroaryl-, cycloalkyl-, halogen-, hydroxy-, amino-, carboxy-, formyl-, —O—, —CO— or —CO—O-substituted components, for example phenyl, 2-methylphenyl (2-tolyl), 3-methylphenyl (3-tolyl), 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 4-phenylphenyl, 1-naphthyl, 2-naphthyl, 1-pyrrolyl, 2-pyrrolyl, 3-pyrrolyl, 2-pyridinyl, 3-pyridinyl, 4-pyridinyl or $C_6F_{(5-a)}H_a$ where $0 \leq a \leq 5$.

If the anion is a tetrasubstituted borate (Va) $[BR^aR^bR^cR^d]^-$, all four radicals $R^a$ to $R^d$ in this are preferably identical and are each preferably fluorine, trifluoromethyl, pentafluoroethyl, phenyl, 3,5-bis(trifluoromethyl)phenyl or cyanide (CN). Particularly preferred tetrasubstituted borates (Va) are tetrafluoroborate, tetraphenylborate and tetra[3,5-bis(trifluoromethyl)phenyl]borate.

If the anion is an organic sulfonate (Vb) $[R^e$—$SO_3]^-$, the radical $R^e$ is preferably methyl, trifluoromethyl, pentafluoroethyl, p-tolyl or $C_9F_{19}$. Particularly preferred organic sulfonates (Vb) are trifluoromethanesulfonate (triflate), methanesulfonate, p-toluenesulfonate, nonadecafluorononanesulfonate (nonaflate), dimethylene glycol monomethyl ether sulfate and octylsulfate.

If the anion is a carboxylate (Vc) $[R^f$—$COO]^-$, the radical $R^f$ is preferably hydrogen, trifluoromethyl, pentafluoroethyl, phenyl, hydroxyphenylmethyl, trichloromethyl, dichloromethyl, chloromethyl, trifluoromethyl, difluoromethyl, fluoromethyl, ethenyl (vinyl), 2-propenyl, —OOC—$(CH_2)_n$ where n is 0, 1 or 2, R"—OOC—$(CH_2)_n$ where R" is H or $C_1$-$C_8$-alkyl; CH=CH—COO$^-$, CH=CH—COO—R" where R" is H or $C_1$-$C_8$-alkyl, cis-8-heptadecenyl, $CH_2$—$C(OH)(COOH)$—$CH_2$—$COO^-$ or unbranched or branched $C_1$-$C_{18}$-alkyl, for example methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, heptadecyl. Particularly preferred carboxylates (Vc) are formate, acetate, propionate, butyrate, valerate, benzoate, mandelate, trichloroacetate, dichloroacetate, chloroacetate, trifluoroacetate, difluoroacetate, fluoroacetate.

If the anion is a (fluoroalkyl)fluorophosphate (Vd) $[PF_x(C_yF_{2y+1-z}H_z)_{6-x}]^-$, z is preferably 0. Particular preference is given to (fluoroalkyl)fluorophosphates (Vd) in which z=0, x=3 and $1 \leq y \leq 4$, specifically $[PF_3(CF_3)_3]^-$, $[PF_3(C_2F_5)_3]^-$, $[PF_3(C_3F_7)_3]^-$ and $[PF_3(C_4F_7)_3]^-$.

If the anion is an imide (Ve) $[R^g$—$SO_2$—N—$SO_2$—$R^h]^-$, (Vf) $[R$—$SO_2$—N—CO—$R^j]^-$ or (Vg) $[R^k$—CO—N—CO—$R^l]^-$, the radicals $R^g$ to $R^l$ are, independently of one another, preferably trifluoromethyl, pentafluoroethyl, phenyl, trichloromethyl, dichloromethyl, chloromethyl, trifluoromethyl, difluoromethyl, fluoromethyl or unbranched or branched $C_1$-$C_{12}$-alkyl, for example methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl or dodecyl. Particularly preferred imides (Ve), (Vf) and (Vg) are $[F_3C$—$SO_2$—N—$SO_2$—$CF_3]^-$(bis(trifluoro-methylsulfonyl)imide), $[F_5C_2$—$SO_2$—N—$SO_2$—$C_2F_5]^-$(bis(pentafluoroethylsulfonyl)imide), $[F_3C$—$SO_2$—N—CO—$CF_3]^-$, $[F_3C$—CO—N—CO—$CF_3]^-$ and those in which the radicals $R^g$ to $R^l$ are each, independently of one another, methyl, ethyl, propyl, butyl, phenyl, trichloromethyl, dichloromethyl, chloromethyl, trifluoromethyl, difluoromethyl or fluoromethyl.

If the anion is a methide (Vh)

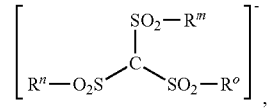

(Vh)

the radicals $R^m$ to $R^o$ are each, independently of one another, preferably trifluoromethyl, pentafluoroethyl, phenyl, trichloromethyl, dichloromethyl, chloromethyl, trifluoromethyl, difluoromethyl, fluoromethyl or unbranched or branched $C_1$-$C_{12}$-alkyl, for example methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl or dodecyl. Particularly preferred methides (Vh) are $[(F_3C$—$SO_2)_3C]^-$(tris(trifluoromethylsulfonyl)methide), $[(F_5C_2$—$SO_2)_3C]^-$(bis(pentafluoroethylsulfonyl)methide) and those in which the radicals $R^m$ to $R^o$ are each, independently of one another, methyl, ethyl, propyl, butyl, phenyl, trichloromethyl, dichloromethyl, chloromethyl, trifluoromethyl, difluoromethyl or fluoromethyl.

If the anion is an organic sulfate (Vi) $[R^pO$—$SO_3]^-$, the radical $R^p$ is preferably a branched or unbranched $C_1$-$C_{30}$-alkyl radical. Particularly preferred organic sulfates (Vi) are methylsulfate, ethylsulfate, propylsulfate, butylsulfate, pentylsulfate, hexylsulfate, heptylsulfate and octylsulfate.

If the anion is a halometalate (Vj) $[M_qHal_r]^{s-}$, M is preferably aluminum, zinc, iron, cobalt, antimony or tin. Hal is preferably chlorine or bromine and very particularly preferably chlorine. q is preferably 1, 2 or 3 and r and s are determined by the stoichiometry and charge on the metal ion.

The anion in formula I is particularly preferably tetrafluoroborate, hexafluorophosphate, trifluoromethanesulfonate, methanesulfonate, formate, acetate, malonate, succinate, anion of phthalic acid or trimellitic acid, mandelate, nitrate, nitrite, trifluoroacetate, sulfate, hydrogensulfate, methylsulfate, ethylsulfate, propylsulfate, butylsulfate, pentylsulfate, hexylsulfate, heptylsulfate, octylsulfate, phosphate, dihydrogenphosphate, hydrogenphosphate, propionate, tetrachloroaluminate, $Al_2C_7$—, chlorozincate, chloroferrate, bis(trifluoromethylsulfonyl)imide, bis(penta-fluoroethylsulfonyl)imide, tris(trifluoromethylsulfonyl)methide, bis(pentafluoroethylsulfonyl)methide, p-toluenesulfonate, bis[salicylato(2-)]borate, tetracarbonylcobaltate, dimethylene glycol monomethyl ether sulfate, octylsulfate, oleate, stearate, acrylate, methacrylate, maleate, hydrogencitrate, vinylphosphonate, bis(pentafluoroethyl)-phosphinate, bis[oxalato(2-)]borate, bis[1,2-benzenediolato(2-)-O,O']borate, dicyanamide, tris(pentafluoroethyl)trifluorophosphate, tris(heptafluoropropyl)trifluorophosphate, tetracyanoborate or chlorocobaltate.

Very particularly preferred anions A in formula I are halides, in particular chloride, alkylsulfonates, in particular C1-C4-alkylsulfonates, particularly preferably methylsulfonate, fully or partially fluorinated carboxylates, in particular trifluoroacetate, and thiocyanate (rhodanide).

General Information Regarding the Salts of the Formula I

The salts of the formula I are preferably ionic liquids, i.e. salts which have a melting point at atmospheric pressure (1 bar) of less than 200° C., in particular less than 100° C., preferably less than 75° C. Very particular preference is given to salts which are liquid at room temperature (21° C.) and atmospheric pressure (1 bar).

Salts of the formula I have, in particular, a molecular weight of less than 1000 g/mol, in particular less than 750 g/mol and particularly preferably less than 500 g/mol.

Particularly preferred salts are imidazolium salts of the formula

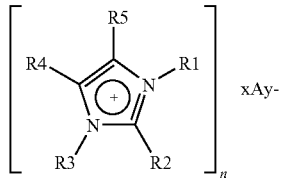

where
R1 and R3 are each, independently of one another, an organic radical having from 1 to 20 carbon atoms,
R2, R4 and R5 are each, independently of one another, an H atom or an organic radical having from 1 to 20 carbon atoms,
A, n, x and y are as defined above and
n, x and y are preferably each 1.
R1 and R3 are each, independently of one another, preferably an organic group comprising from 1 to 10 carbon atoms. This is particularly preferably a hydrocarbon group which does not have any further heteroatoms, e.g. a saturated or unsaturated aliphatic group, an aromatic group or a hydrocarbon group which has both aromatic and aliphatic parts. The group is very particularly preferably a C1-C10-alkyl group, a C1-C10-alkenyl group, e.g. an allyl group, a phenyl group, a benzyl group. In particular, it is a C1-C4-alkyl group, e.g. a methyl group, ethyl group, propyl group, i-propyl group or n-butyl group.

R2, R4 and R5 are each, independently of one another, preferably an H atom or an organic group comprising from 1 to 10 carbon atoms. Particular preference is given to R2, R4 and R5 each being an H atom or a hydrocarbon group which does not have any further heteroatoms, e.g. an aliphatic group, an aromatic group or a hydrocarbon group which has both aromatic and aliphatic parts. Very particular preference is given to an H atom or a C1-C10-alkyl group, a phenyl group or a benzyl group. In particular, the radicals are each an H atom or a C1-C4-alkyl group, e.g. a methyl group, ethyl group, propyl group, i-propyl group or n-butyl group.

A is as defined above and is, in particular, a halide, in particular chloride, alkylsulfonate, in particular a C1-C4-alkylsulfonate, particularly preferably methylsulfonate, a fully or partially fluorinated carboxylate, in particular trifluoroacetate, or thiocyanate (rhodanide).

Regarding the Anion C in Formula II

The anion C in formula II is a carboxylate anion which is different from the anion A.

The carboxylate C is preferably a carboxylate of the formula $$R'—COO^-$$

where
R' is
hydrogen;
$C_1$-$C_7$-alkyl;
—OOC—$(CH_2)_n$— where n is 0, 1 or 2;
R"OOC—$(CH_2)_n$— where n is 0, 1 or 2;
—OOC—CHCH—;
R"OOC—CH═CH—;
ethenyl;
2-propenyl;
a phenyl group which may be unsubstituted or substituted by from one to five groups selected independently from among $C_1$-$C_6$-alkyl, hydroxy, carboxylate (—COO⁻), carboxy (—COOH) and $C_1$-$C_6$-alkyloxycarbonyl (—COOR# where R# is $C_1$-$C_6$-alkyl)
and
R" is hydrogen or $C_1$-$C_6$-alkyl.

The $C_1$-$C_7$-alkyl radical is, for example, methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl or 3-heptyl.

The phenyl group which may be unsubstituted or substituted by from one to five groups selected independently from among $C_1$-$C_6$-alkyl, hydroxy, carboxylate (—COO⁻), carboxy (—COOH) and $C_1$-$C_6$-alkyloxycarbonyl (—COOR² where R² is $C_1$-$C_6$-alkyl) is, for example, phenyl, 2-methylphenyl, 3-methylphenyl, 4-methylphenyl, 2-hydroxyphenyl, 3-hydroxyphenyl, 4-hydroxyphenyl,

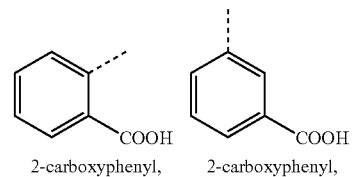

2-carboxyphenyl,    2-carboxyphenyl,

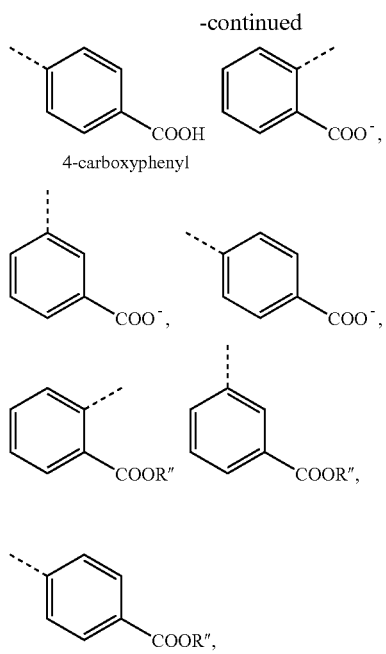
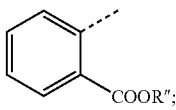

where $R^1$ is $C_1$-$C_6$-alkyl.

The carboxylate of the corresponding heterocyclic quaternary ammonium cation and/or guanidinium cation to be used in the process of the invention preferably comprises, as carboxylate anion, formate, acetate, propionate, butyrate, pentanoate (valerate), hexanoate, heptanoate, octanoate, 2-ethylhexanoate, methyloxalate, ethyloxalate, 1-propyloxalate, 1-butyloxalate, 1-pentyloxalate, 1-hexyloxalate, 1-heptyloxalate, 1-octyloxalate, 1-(2-ethyl)hexyloxalate, methylmalonate, ethylmalonate, 1-propylmalonate, 1-butylmalonate, 1-pentylmalonate, 1-hexylmalonate, 1-heptylmalonate, 1-octylmalonate, 1-(2-ethyl)hexylmalonate, methylsuccinate, ethylsuccinate, 1-propylsuccinate, 1-butylsuccinate, 1-pentylsuccinate, 1-hexylsuccinate, 1-heptylsuccinate, 1-octylsuccinate, 1-(2-ethyl)hexylsuccinate, methylmaleate, ethylmaleate, 1-propylmaleate, 1-butylmaleate, 1-pentylmaleate, 1-hexylmaleate, 1-heptylmaleate, 1-octylmaleate, 1-(2-ethyl)hexylmaleate, methylfumarate, ethylfumarate, 1-propylfumarate, 1-butylfumarate, 1-pentylfumarate, 1-hexylfumarate, 1-heptylfumarate, 1-octylfumarate, 1-(2-ethyl)hexylfumarate, acrylate, methacrylate, benzoate, 2-methylbenzoate, 3-methylbenzoate, 4-methylbenzoate, 2-hydroxybenzoate (salicylate), 3-hydroxybenzoate, 4-hydroxybenzoate, o-hydrogenphthalate, m-hydrogenphthalate, p-hydrogenphthalate, o-phthalate, m-phthalate, p-phthalate, o-methylphthalate, o-ethylphthalate, o-(1-propyl)phthalate, o-(1-butyl)phthalate, o-(1-pentyl)phthalate, o-(1-hexyl)phthalate, o-(1-heptyl)phthalate, o-(1-octyl)phthalate, o-(1-(2-ethyl)hexyl)-phthalate, m-methylphthalate, m-ethylphthalate, m-(1-propyl)phthalate, m-(1-butyl)phthalate, m-(1-pentyl)phthalate, m-(1-hexyl)phthalate, m-(1-heptyl)phthalate, m-(1-octyl)phthalate, m-(1-(2-ethyl)hexyl)phthalate, p-methylphthalate, p-ethylphthalate, p-(1-propyl)phthalate, p-(1-butyl)phthalate, p-(1-pentyl)phthalate, p-(1-hexyl)phthalate, p-(1-heptyl)phthalate, p-(1-octyl)phthalate, p-(1-(2-ethyl)hexyl)phthalate.

The carboxylate C is particularly preferably one in which R' is hydrogen;
methyl;
ethyl;

where
R" is $C_1$-$C_4$-alkyl.

The carboxylate C is very particularly preferably a formate, acetate or propionate, in particular an acetate.

Regarding the Process

There are various methods of preparing ionic liquids.

Ionic liquids, in particular imidazolium salts, can be obtained by means of a single-stage or multistage reaction of starting compounds selected from among: α-dicarbonyl compounds, amino compounds, carbonyl compounds, ammonia and carbonate compounds.

A known preparative process is, for example, the carbonate method which is described in WO 2005/021484.

In the carbonate method, imidazolium salts are obtained by reaction of an α-dicarbonyl compound, a carbonyl compound (in general formaldehyde), an amino compound and ammonia in a first step and a subsequent reaction of the reaction product with a carbonate (in general dimethyl carbonate) in a second step.

A further process for preparing imidazolium salts has been described by Arduengo et al. (WO 91/14678, Arduengo process). In this single-stage process, the preparation is effected by reaction of an α-dicarbonyl compound, a carbonyl compound (in general formaldehyde) and an amino compound in the presence of an acid.

The above processes give carboxylates. If ionic liquids or imidazolium salts having other anions (including other carboxylates) are desired, anion exchange is subsequently carried out.

The anion exchange is carried out as described in WO 2006/27070 by reaction with a protic acid of the desired anion A.

According to the invention, the exchange with the ammonium salt of the anion A or with the protic acid of the anion A is carried out in the presence of ammonia.

Ammonia can, for example, be added beforehand to the protic acid or to the compound having the anion A to be introduced or be added to the mixture of the protic acid and the compound having the anion C to be replaced.

The reaction with the ammonium salt or with the protic acid in the presence of the ammonium salt is preferably carried out at from 0° C. to 100° C., in particular from 10 to 60° C., and atmospheric pressure.

During or after the reaction, the resulting ammonium salt of the anion C (ammonium carboxylate) or ammonia and the corresponding protic acid of the carboxylate can be removed from the reaction mixture, e.g. by distillation.

Customary distillation processes known to those skilled in the art are suitable. A large ratio of vaporizer surface area to liquid volume is advantageous. Distillations using thin film evaporators, falling film evaporators or short path distillations (molecular distillation) are therefore particularly useful.

The surface temperature is preferably from 110 to 300° C., particularly preferably from 130 to 280° C. and very particularly preferably from 140 to 260° C.

The pressure in the region between the vaporizer surface and condenser surface is preferably from 0.0001 to 10 mbar, more preferably from 0.001 to 5 mbar, particularly preferably from 0.05 to 5 mbar.

The process can be carried out continuously or batchwise.

The process of the invention makes it possible to achieve complete anion exchange in a simple manner. Exchange occurs successfully in a single reaction step; more frequent repetition of the distillation to achieve complete anion exchange is no longer necessary.

EXAMPLES

Comparative examples C1 to C3

198 g (1 mol) of BMIM OAc (1-butyl-3-methylimidazolium acetate) are placed in a round-bottom flask which has been made inert and is provided with a dropping funnel and reflux condenser. The amount of acid indicated in the appended table is added slowly while stirring, with the temperature being kept below 50° C. (an exothermic reaction is observed during the addition; the temperature is kept down either by appropriately slow addition with air cooling or by cooling with water).

After cooling to room temperature, the major part of the volatile constituents is taken off at a pressure of 0.1 mbar, with the internal temperature being increased to 120° C. When no more low boilers are given off from the mixture under these conditions, the mixture is cooled and nitrogen is admitted. The residue is transferred to the reservoir of the short-path distillation and fed in at a rate of 100 ml/h at the evaporator temperature indicated below. The pressure in the short-path distillation is set to 0.05 mbar. The product is obtained as bottom output, so that the short-path distillation here functions as a very efficient form of low boiler stripping.

The condensed low boilers comprise water (when an aqueous reagent is added) and acetic acid.

| No. | Acid | BMIM OAc:acid mol:mol | Evaporator temp. ° C. | Product (salt having the new anion) | Yield % | Purity* |
|---|---|---|---|---|---|---|
| C1 | HCl; 35% in water | 1:1.033 | 170 | BMIM Cl | 93.5 | comprises 20 mol % of HOAc after first passage<br>comprises 3 mol % of HOAc after second passage |
| C2 | CF3COOH (trifluoroacetic acid) | 1:1.017 | 150 | BMIM TFA | 90.9 | comprises 13 mol % of HOAc after first passage<br>comprises 4 mol % of HOAc after second passage |
| C3 | CH3SO3H (methanesulfonic acid) | 1:1.005 | 170/190 | BMIM CH3SO3 | 92.3 | comprises 9 mol % of HOAc after first passage<br>no HOAc after the second passage |

*Analysis by H-NMR

Examples E1 to E4

According to the Invention 198 g (1 mol) of BMIM OAc are placed in a round-bottom flask which has been made inert and is provided with a dropping funnel and reflux condenser. The ammonium salt indicated in the appended table is added slowly while stirring, with the temperature being kept below 50° C. (an exothermic reaction is observed during the addition; the temperature is kept down either by appropriately slow addition with air cooling or by cooling with water).

After cooling to room temperature, the major part of the volatile constituents is taken off at a pressure of 3 mbar, with the internal temperature being increased to 130° C. When no more low boilers are given off from the mixture under these conditions, the mixture is cooled and nitrogen is admitted. The residue is transferred to the reservoir of the short-path distillation and fed in at a rate of 100 ml/h at the evaporator temperature indicated below. The pressure in the short-path distillation is set to 0.05 mbar. The product is obtained as bottom output, so that the short-path distillation here functions as a very efficient form of low boiler stripping.

| No. | Salt | BMIM OAc:salt mol:mol | Evaporator temp. ° C. | Product salt with new anion | Yield % | Purity* |
|---|---|---|---|---|---|---|
| E1 | NH4 SCN | 1:1.011 | 160 | BMIM SCN | 86.9 | >95% (H-NMR) |
| E2 | NH4Cl | 1:1.013 | 200 | BMIM Cl | 85.6 | >95% (H-NMR) |
| E3 | NH4 CF3 COO | 1:1.01 | 155 | BMIM CF3COO | 82.1 | >95% (H-NMR) |
| E4 | NH4 MeSO3 | 1:1.02 | 190 | BMIM MeSO3 | 92.3 | >95% (H-NMR) |

*H-NMR

Examples E5 to E7

According to the Invention 198 g (1 mol) of BMIM OAc are placed in a round-bottom flask which has been made inert and is provided with a dropping funnel and reflux condenser. The amount of acid indicated in the appended table and then the indicated amount of ammonia solution (25% by weight in water) are added slowly while stirring, with the temperature being kept below 50° C. in each case (an exothermic reaction is observed during the addition; the temperature is kept down either by appropriately slow addition with air cooling or by cooling with water).

After cooling to room temperature, the major part of the volatile constituents is taken off at a pressure of 3 mbar, with the internal temperature being increased to 130° C. When no more low boilers are given off from the mixture under these conditions, the mixture is cooled and nitrogen is admitted. The residue is transferred to the reservoir of the short-path distillation and fed in at a rate of 100 ml/h at the evaporator temperature indicated below. The pressure in the short-path distillation is set to 0.05 mbar. The product is obtained as bottom output, so that the short-path distillation here functions as a very efficient form of low boiler stripping.

| No. | Acid | BMIM OAc:acid:NH$_3$ mol:mol:mol | Evaporator temp. ° C. | Product | Yield % | Purity* |
|---|---|---|---|---|---|---|
| E5 | HCl (35% in water) | 1:1.02:1.01 | 200 | BMIM Cl | 91 | >95% (H-NMR) |
| E6 | CF3COOH | 1:1.01:1.02 | 155 | BMIM CF3COO | 87 | >95% (H-NMR) |
| E7 | MeSO3H | 1:1.03:1.01 | 190 | BMIM MeSO3 | 95 | >95% (H-NMR) |

*H-NMR

Examples E8 and E9

According to the Invention 170 g (1 mol) EMIM OAc (1-ethyl-3-methylimidazolium acetate) are placed in a round-bottom flask which has been made inert and is provided with a dropping funnel and reflux condenser. The ammonium salt indicated in the appended table is added slowly while stirring, with the temperature being kept below 50° C. (an exothermic reaction is observed during the addition; the temperature is kept down either by appropriately slow addition with air cooling or by cooling with water).

After cooling to room temperature, the major part of the volatile constituents is taken off at a pressure of 3 mbar, with the internal temperature being increased to 130° C. When no more low boilers are given off from the mixture under these conditions, the mixture is cooled and nitrogen is admitted. The residue is transferred to the reservoir of the short-path distillation and fed in at a rate of 100 ml/h at the evaporator temperature indicated below. The pressure in the short-path distillation is set to 0.05 mbar. The product is obtained as bottom output, so that the short-path distillation here functions as a very efficient form of low boiler stripping.

| No. | Salt | EMIM OAc:salt mol:mol | Evaporator temp. ° C. | Product | Yield % | Purity* |
|---|---|---|---|---|---|---|
| E8 | NH4SCN | 1:1.011 | 160 | EMIM SCN | 93 | >95% (H-NMR) |
| E9 | NH4 CF3COO | 1:1.01 | 155 | EMIM CF3COO | 87 | >95% (H-NMR) |

*H-NMR

Examples E10 to E12

According to the Invention 184 g (1 mol) EEIM OAc (1,3-diethylimidazolium acetate) are placed in a round-bottom flask which has been made inert and is provided with a dropping funnel and reflux condenser. The amount of acid indicated in the appended table and then the indicated amount of ammonia solution (25% by weight in water) are added slowly while stirring, with the temperature being kept below 50° C. in each case (an exothermic reaction is observed during the addition; the temperature is kept down either by appropriately slow addition with air cooling or by cooling with water).

After cooling to room temperature, the major part of the volatile constituents is taken off at a pressure of 3 mbar, with the internal temperature being increased to 130° C. When no more low boilers are given off from the mixture under these conditions, the mixture is cooled and nitrogen is admitted. The residue is transferred to the reservoir of the short-path distillation and fed in at a rate of 100 ml/h at the evaporator temperature indicated below. The pressure in the short-path distillation is set to 0.05 mbar. The product is obtained as bottom output, so that the short-path distillation here functions as a very efficient form of low boiler stripping.

| No. | Acid | EEIM OAc:acid:NH3 Mol:mol:mol | Evaporator temp. ° C. | Product | Yield % | Purity* |
|---|---|---|---|---|---|---|
| E10 | HCl (35% in water) | 1:1.01:1.01 | 200 | EEIM Cl | 89 | >95% (H-NMR) |
| E11 | CF3COOH | 1:1.02:1.03 | 155 | EEIM CF3COO | 96 | >95% (H-NMR) |
| E12 | MeSO3H | 1:1.03:1.01 | 190 | EEIM MeSO3 | 93 | >95% (H-NMR) |

*HNM-R

The invention claimed is:

1. A process for preparing salts of the formula I $$(B^+)_n xA^{y-} \quad (I)$$

where
B is a cation comprising at least one nitrogen atom,
A is an anion and
n is an integer from 1 to 3, wherein
x and y are each an integer from 1 to 3 and the product of x and y is equal to n,
by reacting salts of the formula II $$(B^+)_n xC^{y-} \quad (II)$$

where B and n, x and y are as defined above and C is a compound which has one or more carboxylate groups and is different from A,
with the ammonium salt of the anion A or with the protic acid of the anion A in the presence of ammonia.

2. The process according to claim 1, wherein the cation B in formula I is a guanidinium compound or an ammonium compound.

3. The process according to claim 1, wherein the cation B comprises a heterocyclic ring system having at least one nitrogen atom.

4. The process according to claim 1, wherein the cation is an imidazolium cation.

5. The process according to claim 1, wherein the anion is chloride, trifluoroacetate, methylsulfonate or thiocyanate.

6. The process according to claim 1, wherein the salt of the formula I is an imidazolium salt of the formula III

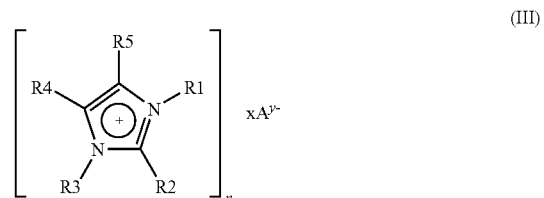

where
A and n, x and y are as defined above,
R1 and R3 are each, independently of one another, an organic radical having from 1 to 20 carbon atoms and
R2, R4 and R5 are each, independently of one another, an H atom or an organic radical having from 1 to 20 carbon atoms.

7. The process according to claim 1, wherein the carboxylate C in formula II is a compound having from 1 to 20 carbon atoms and from one to three carboxylate groups.

8. The process according to claim 1, wherein the carboxylate C in formula II is an anion of a C1-C10-alkanecarboxylic acid.

9. The process according to claim 1, wherein the salt of the formula II is reacted with the ammonium salt of the anion A.

10. The process according to claim 1, wherein the salt of the formula II is reacted with the protic acid of the anion A in the presence of ammonia.

11. The process according to claim 10, wherein the reaction is carried out using a solution comprising ammonia and the protic acid of the anion A.

12. The process according to claim 1, wherein the ammonium salt of the anion C (ammonium carboxylate) or ammonia and the protic acid corresponding to the carboxylate is/are separated off by distillation during or after the reaction.

* * * * *